United States Patent [19]

Smith et al.

[11] Patent Number: 5,013,762
[45] Date of Patent: May 7, 1991

[54] METHOD FOR THE TREATMENT OF NEMATODES IN SOIL USING BROMONITROMETHANE

[75] Inventors: Roger E. Smith; Scott Thornburgh, both of West Lafayette, Ind.; Rodrigo Rodriquez-Kabana, Auburn, Ala.

[73] Assignee: Great Lakes Chemical Corporation, West Lafayette, Ind.

[21] Appl. No.: 442,314

[22] Filed: Nov. 28, 1989

[51] Int. Cl.$^5$ .............................................. A01N 33/18
[52] U.S. Cl. .................................................... 514/740
[58] Field of Search ........................................ 514/740

[56] References Cited

U.S. PATENT DOCUMENTS 2,763,962  9/1956  Hardy .................................. 514/741
2,916,855  12/1959  Thiegs ................................. 514/740
3,445,576  5/1969  Kenaga ............................... 514/740

OTHER PUBLICATIONS

Guide Lines for the Control of Plant Diseases and Nematodes; U.S. Dept. of Agri., Handbook 656, May 1986.

Primary Examiner—Allen J. Robinson
Attorney, Agent, or Firm—Woodard, Emhardt, Naughton, Moriarty & McNett

[57] ABSTRACT

A method for the treatment of nematodes includes the impregnation of soil with a nematicidal amount of bromonitromethane. The application is made at rates of 1 to 40 quarts of bromonitromethane per acre of soil. The bromonitromethane has excellent nematicidal effect at surprisingly low concentrations, is cost effective, and is not phytotoxic. The bromonitromethane may be suspended in a variety of liquid or solid carrier systems, and is applied to the soil by methods including mixing, fumigation and injection.

24 Claims, No Drawings

METHOD FOR THE TREATMENT OF NEMATODES IN SOIL USING BROMONITROMETHANE

BACKGROUND OF THE INVENTION

Field of the Invention:

This invention relates to the field of methods and chemicals for the treatment of nematodes in soil, and particularly to a method using bromonitromethane which proves to be highly efficacious as a nematicide at low levels.

Description of the Prior Art:

Nematodes are slender, worm-like organisms found in the soil almost anywhere in the world. Most nematodes range from one-fiftieth to one-twenty-fifth inches long. Nematodes reproduce by eggs and typically progress through four larval stages to adulthood.

Some nematodes are plant parasitic, and more than one thousand species of nematodes are known to be harmful to plants. Many plants are affected by nematodes, including soybeans, peanuts, cotton, tobacco, strawberries, root crop, ornamentals, citrus, vegetables and many other crops. Nematodes feed on the roots and lower stems of plants, and some attack the leaves and flowers. Some species of nematodes inadvertently introduce pathogenic, root-invading microorganisms into the plants while feeding. Nematodes may also predispose plant varieties to other disease causing agents, such as wilts and root rots. In other instances, the nematodes themselves cause the disease, disrupting the flow of water and nutrients in the xylem system, resulting in root-knot or deprivation of the above-ground parts, and ultimately causing stunting. Symptoms of nematode infestation include swellings, thickenings, galls and distortions of above-ground components of the plant, and root conditions such as short stubby roots, lesions (dead spots), swellings, galls and general breakdown. See, "The Mutagenicity of Pesticides" by Samuel S. Epstein and Marvin S. Legator, MIT Press, 1971.

The extent of crop loss to nematode infestation is substantial and widespread. Yield losses in agricultural crops in the United States and throughout the world are enormous, and have been labelled as "appalling" by experts in the field. For example, the losses due to nematode infestation for New Jersey alone were estimated as fifteen million dollars in one year, and losses for the entire United States may be as much as five hundred million dollars per year. See, "Handbook on Biological Control of Plant Pests" by Waldimero Coscarelli, Plants & Gardens publication, Vol. 16, No.3, 1960.

There has been a substantial need for chemical controls to limit the damage caused by nematodes and to curb their spread to unifested fields. Nematicides have been available in the prior art, some of which were useful as fumigants. The most effective and widely used control agents have been methyl bromide and EDB (ethylene dibromide), and certain chlorinated compounds including D-D (1,3-dichloropropene,1,2-dichloropropane), DBCP (1,2-dibromo-3-chloropropane), and Telone (1,3-dichloropropene). In U.S. Pat. No. 3,445,576, issused to Kenaga on May 20, 1969, there is disclosed the use of bromodifluoronitromethane for controlling nematodes, insects and fungi. Other nematicides generally fall within three groups: (1) organophosphate insecticides, (2) isothiocyanates, and (3) carbamate or oxime insecticides. For example, Vapam (sodium N-methyl dithiocarbamate) has proven to be useful, especially as a pre-plant treatment.

Some of the better known nematicides have been in use for many years. The nematicidal properties of DD and EDB, for example, were discovered in 1943 and 1945 and effectively launched the use of volatile nematicides on a field-scale basis. Previously only seedbeds, greenhouse beds, and potting soil had been treated, with materials such as chloropicrin (trichloronitromethane), carbon disulfide and formaldehyde. These were very expensive, in some instances explosive, and usually required a surface seal because of their relatively high vapor pressures. See, "The Pesticide Book" by George W. Ware, W. H. Freeman & Co., 1978.

Many of the time-tested nematicides, however, have fallen by the wayside because of carcinogenicity, toxicity and environmental problems. DBCP, for example, was found to be relatively cheap and effective, but has been cancelled as a carcinogen. Methyl bromide is lethal to all plant and animal life, and is classified as a sterilant which should be used at least two weeks before planting to avoid its total phytotoxic effect. Attempts to substitute non-fumigants, dithiocarbamates and methyl isothiocyanates have been mostly unsuccessful because of the expense and the limited efficacy of those materials.

Reference to other chemical pesticides has not proven to be very helpful. There are numerous forms of pesticides adapted to the treatment of particular pests. These include, for example, insecticides, herbicides, fungicudes, rodenticides, bactericides, acaricides, algicides, miticides, molluscicides, avicides, slimicides, piscicides and ovicides, as well as disinfectants, growth regulators, defoliants, desiccants, repellents, attractants and chemosterilants. The operation of the different types of pesticides varies according to the pests being treated. For example, the known or suspected major modes of chemicals for treating plants (including herbicides, fungicides, etc.) include: (a) inhibition of photosynthesis, (b) inhibition of oxidative phosphorylation, (c) hormone analogs, (d) inhibition of pantothenate synthesis and (e) inhibition of porphyrin, hence of chlorophyll synthesis. In contrast, the operation of chemicals for the treatment of animals (insecticides, nematicides, etc.) include: (a) inhibition of acetylcholinesterase, (b) inhibitions of neuromuscular junction and (c) neurotoxication. There have consequently been a vast number of known pesticides covering a large variety of chemicals operating in differing fashions. However, few effective nematicides have been discovered in the prior art.

There has therefore remained a longstanding and substantial need for a nematicide which is effective, and does not have the disadvantages of the prior art chemicals. The elimination of cheap, effective fumigant nematicides and the poor performance of remaining controls are forcing some crops out of production in the traditional nematode-infested areas of the United States. Also, some nematodes are beginning to spread to new areas never before troubled by these pests, as evidenced by the appearance of the soybean cyst nematode in the midwestern United States. While the need continues to grow, concerns over the inherent toxicity of contact nematicides, and environmental problems from high rates of application (such as leaching into ground water) will undoubtedly result in the restriction or elimination of some or all of the remaining know products.

The present invention is based upon the discovery that bromonitromethane is highly effective as a nematicide, particularly as a fumigant, and does not have the high expense or toxicity associated with certain prior art compounds. Heretofore, bromonitromethane was long ago indicated to be useful only as a fungicide, as disclosed in U.S. Pat. No. 2,763,962, issued to Hardy on Sept. 25, 1956. However, it is believed that this chemical was never given governmental approval or used commercially, and that no other uses for the chemical have been described until now.

SUMMARY OF THE INVENTION

Briefly describing one aspect of the present invention, there is provided a method for treating nematodes which includes impregnating the soil with a nematicidal amount of bromonitromethane. Bromonitromethane is applied by a variety of methods, such as fumigation, and may be suspended in a suitable carrier system.

It is an object of the present invention to provide a highly effective and cost-efficient method for the treatment of nematodes.

Another object of the present invention is to provide a method for treating nematode-infested soil, which method is readily accomplished by fumigation or the like and is active against adult nematodes, their larvae, and the eggs.

A further object of the present invention is to provide a method for controlling nematodes which utilizes a highly effective nematicide which may be applied at relatively low rates, thereby minimizing the potential for toxicity and environmental concerns.

It is another object of the present invention to provide a method for treating nematodes which avoids disadvantages of prior art chemicals and methods such as low efficacy, high cost and potential toxicity.

Further objects and advantages of the present invention will be apparent from the description of the preferred embodiment which follows.

DESCRIPTION OF THE PREFERRED EMBODIMENT

For the purposes of promoting an understanding of the principles of the invention, reference will now be made to the preferred embodiments thereof and specific language will be used to describe the same. It will nevertheless be understood that no limitation of the scope of the invention is thereby intended. Alterations and further applications of the principles of the invention one contemplated as would normally occur to one skilled in the art to which the invention relates.

There has remained a substantial and long felt need for a nematicide which has the combined advantages of high efficacy, low cost and low toxicity to humans. Various nematicides have been provided in the prior art, but these have generally been deficient in one or more of these areas. In fact, several prior art nematicides have been banned or severely restricted as to use, and others are unacceptably low in efficacy or high in cost. With the considerable losses in crop yield which are attributable to nematicide infestation, the need for a useful nematicide has continued.

The present invention involves the impregnation of soil with a nematicidal amount of bromonitromethane. The chemical itself has been known for over thirty six years, having been described in U.S. Pat. No. 2,632,776, issued to Slagh on Mar. 24, 1953. However, the present invention is based on the unexpected discovery that bromonitromethane is a highly-effective nematicide. It is useful in surprisingly low amounts for the control of all stages of nematodes, and is particularly effective and cost-efficient when used as a fumigant.

The production of bromonitromethane is described in the previously-referenced Slagh patent. The disclosure of this patent as to a method of producing this compound is incorporated herein by reference. The production of bromonitromethane is within the ordinary skill in the art, and further description as to methods for its production is therefore unnecessary. Bromonitromethane is a colorless liquid boiling at about 146°–148° C. at 750 mm Hg and having a specific gravity of 2.007 at 25° C. The compound is somewhat soluble in many organic solvents and water. Bromonitromethane is a mild lacrimator, and therefore serves as a warning agent to limit accidental human exposure. No threat of carcinogenicity or other chronic pathology is known for the chemical, and does not leave phytotoxic residue in soil after fumigation.

Bromonitromethane has been found to be useful in controlling nematodes, even when applied in limited quantities to infested soil. As used herein, the term "soil" is intended to encompass any plant growth medium. The rate of use may vary somewhat with the nature of the soil, including density, porosity, etc. Also, the rate may vary according to the species of nematodes, the degree of infestation, and the manner of application of the bromonitromethane. It has been determined, however, that bromonitromethane is highly volatile and will therefore permeate the soil rapidly and widely. As demonstrated in the specific examples herein, bromonitromethane is effective against adult nematodes, their larval forms, eggs, and cysts.

The bromonitromethane is applied to the nematode-infested soil by a variety of methods. The chemical is particularly useful as a fumigant due to its high volatility and permeability into the soil. Exposure of nematodes to vapors of bromonitromethane has been found to be sufficient to destroy the nematodes. Use of the chemical as a fumigant is advantageous in obtaining a quick and thorough distribution of the bromonitromethane to the infested site. In addition, the bromonitromethane may be impregnated into the soil by other conventional means, including mixing or injection into the soil. In certain applications the bromonitromethane may be preheated prior to application to enhance its distribution, particularly when applied at low ambient or soil temperatures. Also, the chemical may be applied with or without the presence of a plastic cover. These and other variations for the administration of soil treatment chemicals, particularly fumigants, will be readily appreciated by those skilled in the art and are applicable to the present invention.

For the various methods of application, the bromonitromethane may be combined with suitable carrier systems of either liquid or solid form. For example, liquid compositions may be formulated by dissolving the bromonitromethane in suitable organic solvents, including acetone, toluene, methylene chloride and petroleum distillates. Alternatively, aqueous compositions may be prepared by dispersing the bromonitromethane in water with the use of appropriate dispersing and/or emulsifying agents, with or without water immiscible solvents. For example, such agents may include the condensation products of alkylene oxides with phenols and organic acids, polyoxyethylene derivatives or sorbitan esters, alkyl aryl sulfonates, complex ether alcohols and the like. The bromonitromethane, directly or in a volatile organic solvent solution, may also be absorbed into solid carriers including granular, dust or other finely divided solids such as chalk, talc, pyrophyllite, attapulgite, fuller's earth or bentonite. These and other suitable carrier systems of the foregoing types are known in the art and may be determined without undue experimentation by those skilled in the art. The resultant compositions of bromonitromethane and carrier may be directly applied to the soil, or may be prepared in a concentration for subsequent dilution with inert chemicals (such as water for the aqueous dispersion) prior to use.

The bromonitromethane is applied to the soil in a nematicidal amount. The level of application, depending on several factors, is preferably established in terms of the amount which provides the desired nematicidal effect under the use conditions. For example, the preferred usage is at the minimum nematicidal rate. Good results are obtained when the bromonitromethane is present in the soil in an amount between 2 and 80 parts (w/w) of bromonitromethane per million parts of the soil. A preferred rate of application is between 4 and 40 parts (w/w) of bromonitromethane per million parts of the soil. A particularly advantageous balance between efficacy and amount of chemical used is obtained at about 8 parts (w/w) of bromonitromethane per million parts of the soil. It is a feature of the present invention that the bromonitromethane is efficacious when used at low levels, namely less than about sixteen ppm (w/w) in soil.

The bromonitromethane is advantageously applied to soil at a rate of between 0.02 and 1.0 ml of bromonitromethane per kilogram of soil. In a preferred embodiment, the soil is treated with between 0.04 and 0.5 ml of bromonitromethane per kilogram of soil. A most preferred rate of application is about 0.1 ml of bromonitromethane per kg of soil. One aspect of the present invention is that the bromonitromethane is effective at rates below about 0.2 ml per kg of soil. Such applications may be made in any of the variety of methods already described.

In field applications, the bromonitromethane is applied to the soil to treat the surface layer in which the nematodes may reside. Typically, the treatment is directed at the top several inches of soil, perhaps as little as a few inches or as much as ten to twelve inches. The bromonitromethane is preferably injected at a depth of 7-10 inches or deeper. The amount of bromonitromethane applied to the soil is efficaciously in the range of 1 to 40 quarts per acre of soil. A more preferred application rate is between 2 and 20 quarts of bromonitromethane per acre of soil, with the most preferred rate being about 4 quarts per acre. The bromonitromethane may be desirably used at rates as low as below about 8 quarts per acre.

It will be appreciated that the selected method and rate of application will depend somewhat on the conditions of the soil, the crop and the infestation. The underlying consideration is the application of a nematicidal amount of bromonitromethane, i.e., an amount of bromonitromethane which will give the desired nematicidal effect under the conditions of use. The desired amount may be affected by the method of application, the temperature or other conditions of the soil or air, the form of the composition (liquid, solid or vapor), and the ingredients of the composition. The selected rate may also be affected by the nature of the infestation, including the species of nematodes, the condition of the nematodes (encysted, etc.), and the extent of infestation. Generally, the bromonitromethane has been found not to leave soil residues harmful to plants.

The compound may be used prior to planting or at planting time. For transplanted crops (e.g., tobacco), fumigants are usually applied two weeks or more before planting. For seeded crops (soybean, peanut, cotton, etc.), application at planting time is usually acceptable. In some applications, fumigant, seed and fertilizer are applied in one application system.

The bromonitromethane may be prepared in concentrated form for later application upon dilution. Suitable carriers, particularly those providing an aqueous system, may be prepared in this manner. The concentration of the bromonitromethane composition, including liquid and solid forms, may also be adjusted to match the method of application in order to provide the desired distribution of bromonitromethane in the soil. The concentration of bromonitromethane in the soil is the determining factor, and the concentration of the composition being applied is therefore not critical and may range widely. However, it has been found that an example of a suitable composition, including bromonitromethane in a carrier system, may have a concentration from 100% down to 25% of the composition. These ranges, however, are illustrative only, and are not to be taken as limiting in nature.

Various other modifications may be made to the bromonitromethane compositions described. One form of the invention is a composition consisting only of bromonitromethane or only of the bromonitromethane and an inert carrier system. However, additional chemicals not inconsistent with the bromonitromethane or the given carrier system may be included in the composition. Other active ingredients such as herbicides, fungicides, insecticides and other pesticides may be included. In any combination, the ability to add other chemicals can be readily determined, with a basic consideration being that the chemicals be compatible with bromonitromethane and not interfere with its nematicidal activity.

The unexpected and significant efficacy of bromonitromethane as a nematicide is illustrated by the following examples.

EXAMPLE 1

A test composition containing bromonitromethane was prepared by combining bromonitromethane with acetone. The resulting Test Composition contained two (2) ml of bromonitromethane per twenty (20) ml of the Test Composition. For the examples hereafter, this Test Composition was added to the soil samples in amounts sufficient to achieve the indicated levels of bromonitromethane in the soil mix.

EXAMPLE 2

A test was conducted to demonstrate the efficacy of a composition containing bromonitromethane ("BNM") for the treatment of nematodes. Soil was collected from a field located on the Auburn University Experiment Station at Headland, Ala. This field was selected as being naturally infested with various types of nematodes, namely *Meloidogyne arenaria* and *M. incognita* (root-knot), *Heterodera glycines* (soybean cyst), *Pratylenchus brachyurus* (lesion), *Helicotylecnchus dihystera* (spiral) and also the non-parasitic nematodes Aphelenchus spp., Dorylaimida and saprophytic or microbivorous (mostly Rhabditida).

The soil was placed in containers, and received treatment with various rates of experimental substances. Treatments were mixed directly into the soil. The Control samples received no treatments. A positive control was provided by treating a third set of samples with the granular, systemic nematicide Temik 15G (alkicarb) at its prescribed rate of 60 ml/kg soil. Test samples were also prepared by mixing different concentrations (0.1, 0.5 and 1.0 ml/kg soil) of bromonitromethane with the sample soil. The containers were arranged in a randomized complete block design with eight replications. One week after treatment, 100 grams of soil were removed from each container and assayed for populations of nematodes. Standard incubation techniques were used for enumeration of nematode populations.

Good results were obtained for the treatment with bromonitromethane of the various species of nematodes. As shown in Table 1, the bromonitromethane at all rates of application killed all larvae of the root-knot nematode. Treatments with bromonitromethane also killed all lesion, Dorylaimoid and saprophagous nematodes present in the soil. The controls showed that, absent treatment, viable populations of nematodes were present in the soil. The comparison nematicide Temik showed no activity in the test, apparently because it had insufficient time to act on the nematodes.

Bromonitromethane applied directly to soil at the rates of 0.1, 0.5 and 1.0 ml/kg soil, killed the larvae of root-knot nematodes. The treatments also killed adult larvae of lesion, Dorylaimoid and saprophagous nematodes. Repetition of this same test with application rates of 0.02, 0.04, 0.2 and 0.4 ml bromonitromethane per kg of soil provides similarly good results.

TABLE 1

| Treatment | ml/kg soil | Root-Knot Larvae | Lesion Nematodes | Dorylaimoid Nematodes | Saprophagous Nematodes |
|---|---|---|---|---|---|
| Control | — | 49.3 | 39.4 | 8.3 | 264.0 |
| Temik 15G | 60.0 | 58.9 | 39.4 | 7.6 | 108.6 |
| BNM | 0.1 | 0.0 | 0.0 | 0.0 | 0.0 |
| BNM | 0.5 | 0.0 | 0.0 | 0.0 | 0.0 |
| BNM | 1.0 | 0.0 | 0.0 | 0.0 | 0.0 |

EXAMPLE 3

Example 3 was conducted exactly as Example 2, with the exceptions that a different soil and different control treatments were used. In Example 3, soil was collected from a field on the Auburn University Experiment Station at Monroeville, Ala. In addition to the other types of nematodes, this soil contained the soybean cyst nematode. This nematode forms resistant cysts in the soil and is considered extremely difficult to kill.

The results of Example 3 are contained in Table 2, which shows that all nematodes were killed by applications of the test solution at a rate sufficient to achieve a concentration of the bromonitromethane of 0.04 ml/kg soil and higher. Some nematodes survived applications at 0.01 and 0.02 ml/kg soil, although the bromonitromethane even at these lower levels showed a marked nematicidal effect.

At rates of application ranging from 0.01 to 0.1 ml/kg soil, the bromonitromethane killed root-knot nematode larvae, encysted root-knot nematodes and their eggs. Cyst, lesion, spiral, Aphelenchus, Dorylaimoid and saprophagous nematodes, encysted soybean cyst nematodes, and their larvae and eggs, were also killed.

TABLE 2

| Treatment | ml/BNM /kg Soil | Root-Knot Larvae | Cyst Nema. | Lesion Nema. | Spiral Nema. | Aphel. Nema. | Dory. Nema. | Sapro. Nema. |
|---|---|---|---|---|---|---|---|---|
| Control (Acetone) | — | 37.4 | 241.4 | 41.5 | 165.4 | 10.0 | 11.3 | 231.5 |
| | 0.01 | 1.5 | 185.6 | 16.1 | 0.4 | 0.0 | 0.0 | 30.6 |
| | 0.02 | 0.3 | 8.0 | 0.6 | 0.0 | 0.0 | 0.0 | 5.4 |
| | 0.04 | 0.0 | 0.0 | 0.0 | 0.0 | 0.0 | 0.0 | 0.0 |
| | 0.05 | 0.0 | 0.0 | 0.0 | 0.0 | 0.0 | 0.0 | 0.0 |
| | 0.06 | 0.0 | 0.0 | 0.0 | 0.0 | 0.0 | 0.0 | 0.0 |
| | 0.08 | 0.0 | 0.0 | 0.0 | 0.0 | 0.0 | 0.0 | 0.0 |
| | 0.1 | 0.0 | 0.0 | 0.0 | 0.0 | 0.0 | 0.0 | 0.0 |
| Control ($H_2O$) | — | 40.5 | 205.9 | 20.8 | 48.4 | 2.8 | 5.3 | 186.0 |

EXAMPLE 4

Following Examples 2 and 3, the soil remaining in the test containers was planted with squash seeds. After 29 days growth, the plants were uprooted. Measurements of various plant and plant root characteristics were measured and nematode galls were counted. The results for the plantings in the soil samples of Examples 2 and 3 are contained in the following Tables 3 and 4, respectively.

Referring to Table 3, these results show that plant height and weight were increased in response to treatment of the soil with bromonitromethane. The increased growth was due to elimination of plant parasitic nematodes from the soil. Root weight was unaffected by any of the treatments reflected in Table 3. This demonstrates a lack of toxic effects in the soil as a result of treatment with the bromonitromethane. Lack of root toxicity is also shown by the observation that root condition was the same for all treatments and controls.

Galls are symptomatic of the activity of parasitic root-knot nematodes on plant roots. Because all adult nematodes and their larvae were killed by the treatment of Example 2, any galls found represent activity of nematodes which hatched from eggs. The elimination of more than 90 percent of the expected number of root galls evidences the ovicidal activity of the bromonitromethane in the soil. The Gall Rate evaluation showed that root galls present in the bromonitromethane treatments were inconsequential.

Applications of bromonitromethane directly to the soil at the indicated rates were not harmful to the growth of the plants (yellow crookneck squash). Parameters of plant height, plant and root weights and root condition showed no adverse responses to this treatment. Absence of root galls, as reflected by Table 3, indicates that direct application of bromonitromethane to soil at the rates of 0.1, 0.5 and 1.0 ml/kg soil resulted in ovicidal activity to nematode eggs. Application rates of 0.02, 0.04, 0.2 and 0.4 ml bromonitromethane per kg of soil provides similarly good results.

TABLE 3

| Treatment | ml/kg Soil | Top Height (cm) | Top Weight (g) | Root Weight (g) | Root Condition | Galls/Gram Root | Gall Rate |
|---|---|---|---|---|---|---|---|
| Control | — | 18.4 | 2.69 | 0.45 | 4.0 | 38.0 | 4.3 |
| Temik 15G | 60.0 | 19.1 | 3.18 | 0.35 | 4.0 | 0.0 | 0.0 |
| BNM | 0.1 | 21.7 | 3.67 | 0.40 | 4.0 | 0.0 | 0.0 |
| BNM | 0.5 | 21.7 | 2.34 | 0.38 | 4.0 | 0.0 | 1.1 |
| BNM | 1.0 | 21.6 | 2.23 | 0.41 | 4.0 | 2.0 | 0.9 |

Root Condition (Scale: 1 = best; 5 = worst)
Gall Rate (Scale: 0 = no galling; 10 = maximum galling)

Referring to Table 4, similarly good results were achieved upon planting of the soil from Experiment 3. Top height and weight increased with dosages of bromonitromethane up to the rate of 0.1 ml/kg soil, with only a minimal decline at the highest dosage rate. Root weight paralleled the results for the plant tops. Root condition was about the same for all treatments, as expected.

Galls/g root decreased with the rate of treatment, again as expected. This demonstrated control of root-knot nematode eggs. Gall Rating decreased with treatment in agreement with the galls/g root data. Cyst numbers generally decreased with increased rate of application of bromonitromethane. At the rate of 0.05 ml/kg soil and above, no cysts were found. These results demonstrate the efficacy of bromonitromethane for control of encysted soybean cyst nematodes. Rates of application of 0.01 to 0.1 ml of bromonitromethane per kg soil resulted in increased growth of plants as determined by plant height, weight of plants and roots and root condition. Plant growth responses were the direct result of destruction of plant parasitic nematodes, their larvae and their eggs.

of bromonitromethane expressed as ppm of soil. In addition, similarly good results are achieved upon conducting Examples 2 and 3 at levels of 2, 4, 16 and 20 parts (w/w) bromonitromethane per million parts soil.

EXAMPLE 6

The test procedures of Examples 2 and 3 for bromonitromethane levels of 0.1, 0.5 and 1.0 ml/kg approximate corresponding concentrations of 4, 20 and 40 quarts bromonitromethane per acre of soil. Identical results are therefore obtained for these levels of bromonitromethane expressed as quarts per acre of soil. In addition, similarly good results are achieved upon conducting Examples 2 and 3 at levels of 1, 2, 8 and 16 quarts bromonitromethane per acre of soil.

EXAMPLE 7

The Examples 2-6 are repeated with combinations of bromonitromethane in various carrier systems, including (a) organic solvent carriers (b) aqueous emulsions and (c) finely divided solid carriers. Good nematicidal effect of the bromonitromethane is achieved in each instance.

EXAMPLE 8

Example 8 was conducted exactly as Experiment 2, but with the exception that the bromonitromethane was applied to the soil using a fumigation method. An experimental device was used which included test soil received within a container and suspended above an empty chamber. The test soil was separated from the chamber by a fiberglass screen. The test compositions were injected into the chamber and vapors released by the treatment substances penetrated the soil above the chamber, fumigating the soil. The following results were obtained.

Table 5 shows that all nematodes were killed except at the lowest rate of treatment with bromonitromethane. About 90 percent of root-knot nematode larvae were killed by the lowest rate of bromonitromethane tested. This result showed that bromonitromethane had excellent fumigant nematicide activity. Bromonitromethane was also effective as a fumigant on lesion, Dorylaimoid and saprophagous nematodes.

Table 6 shows that application of bromonitromethane

TABLE 4

| Treatment | ml BNM /kg Soil | Top Height (cm) | Top Weight (g) | Root Weight (g) | Root Condition | Gall/g Root | Gall Rate | Cyst No. |
|---|---|---|---|---|---|---|---|---|
| Control (Acetone) | 0.0 | 22.1 | 0.81 | 0.48 | 4.4 | 17.5 | 3.2 | 0.0 |
| | 0.01 | 28.1 | 1.14 | 0.91 | 4.1 | 14.9 | 3.1 | 2.2 |
| | 0.02 | 36.3 | 2.16 | 1.71 | 3.7 | 11.9 | 4.0 | 20.5 |
| | 0.04 | 45.7 | 3.57 | 2.95 | 3.5 | 8.7 | 3.8 | 2.3 |
| | 0.05 | 47.7 | 3.83 | 3.33 | 3.3 | 8.1 | 3.9 | 0.0 |
| | 0.06 | 51.3 | 3.89 | 2.87 | 3.4 | 4.5 | 2.5 | 0.0 |
| | 0.08 | 55.1 | 3.96 | 2.57 | 3.6 | 2.6 | 1.7 | 0.0 |
| | 0.10 | 50.5 | 3.91 | 2.37 | 3.5 | 0.3 | 0.4 | 0.0 |
| Control (H$_2$O) | 0.00 | 38.0 | 1.92 | 0.59 | 4.0 | 32.2 | 4.5 | 0.9 |

Root Condition (Scale: 1 = best; 5 = worst)
Gall Rate (Scale: 0 = no galling; 10 = maximum galling)

EXAMPLE 5

The test procedures of Examples 2 and 3 for bromonitromethane levels of 0.1, 0.5 and 1.0 ml/kg approximate corresponding concentrations of 8, 40 and 80 parts (w/w) bromonitromethane per million parts of soil. Identical results are therefore obtained for these levels as a fumigant had no measurable toxic effects on growth of the plants (crookneck squash). Application rates of 0.05, 0.10, 0.15, 0.20 and 0.25 ml/kg soil, killed all root-knot nematode larvae and eggs, and the adult lesion, Dorylaimoid and saprophagous nematodes. Fumigant activity was achieved without toxic symptoms to the plants.

TABLE 5

| Treatment | ml/kg Soil | Root-Knot Larvae | Lesion Nematodes | Dorylaimoid Nematodes | Saprophagous Nematodes |
|---|---|---|---|---|---|
| Control (Acetone) | — | 20.0 | 5.8 | 7.6 | 63.4 |
| BNM | 0.05 | 1.9 | 2.6 | 0.0 | 10.0 |
| BNM | 0.10 | 0.0 | 0.0 | 0.0 | 0.0 |
| BNM | 0.15 | 0.0 | 0.0 | 0.0 | 0.0 |
| BNM | 0.20 | 0.0 | 0.0 | 0.0 | 0.0 |
| BNM | 0.25 | 0.0 | 0.0 | 0.0 | 0.0 |
| Control (H₂O) | — | 19.3 | 7.6 | 7.6 | 60.4 |

TABLE 6

| Treatment | ml/kg soil | Top Height (cm) | Top Weight (g) | Root Weight (g) | Root Condition | Galls/Gram Root | Gall Rate |
|---|---|---|---|---|---|---|---|
| Control (Acetone) | — | 22.1 | 2.56 | 0.32 | 4.0 | 47.0 | 3.8 |
| BNM | 0.50 | 23.1 | 2.76 | 0.42 | 4.0 | 0.0 | 0.0 |
| BNM | 0.10 | 21.8 | 2.34 | 0.31 | 4.0 | 0.0 | 0.0 |
| BNM | 0.15 | 21.6 | 2.27 | 0.49 | 4.0 | 0.0 | 0.0 |
| BNM | 0.20 | 20.4 | 2.06 | 0.33 | 4.0 | 0.0 | 0.0 |
| BNM | 0.25 | 21.1 | 2.24 | 0.28 | 4.0 | 0.0 | 0.0 |
| BNM | — | 21.8 | 2.58 | 0.24 | 4.0 | 33.0 | 3.2 |

Root Condition (Scale: 1 = best; 5 = worst)
Gall Rate (Scale: 0 = no galling; 10 = maximum galling)

EXAMPLE 9

Repetition of the foregoing Examples using various other carrier systems, as described in Example 7, and for various other plants yields similar results. In addition, the application of the bromonitromethane by other means, such as injection of the soil, to achieve the same levels of bromonitromethane in the soil produces similar good results.

EXAMPLE 10

The bromonitromethane is combined with other chemical treatments including insecticides, fungicides, herbicides, etc. and applied to the soil. Applications in accordance with the various foregoing carrier systems and treatment methods results in effective nematicidal treatment of the soil.

What is claimed is:

1. A method for the treatment of nematodes in soil which comprises applying to the nematodes in the soil a nematicidal amount of bromonitromethane.

2. The method of claim 1 in which said applying comprises impregnating the bromonitromethane into the soil by an application process selected from the group consisting of: mixing, fumigation and injection.

3. The method of claim 2 in which said impregnating comprises fumigating the soil with a nematicidal amount of bromonitromethane.

4. The method of claim 1 and which comprises impregnating the soil with bromonitromethane in the amount of between 2 and 80 parts of bromonitromethane per million parts of the soil.

5. The method of claim 4 in which said impregnating comprises applying the bromonitromethane to the soil by an application process selected from the group consisting of: mixing, fumigation and injection.

6. The method of claim 4 and which comprises impregnating the soil with bromonitromethane in the amount of between 4 and 40 parts of bromonitromethane per million parts of the soil.

7. The method of claim 6 and which comprises impregnating the soil with bromonitromethane in the amount of about 8 parts of bromonitromethane per million parts of the soil.

8. The method of claim 4 and which comprises impregnating the soil with bromonitromethane in the amount of less than about 16 parts of bromonitromethane per million parts of the soil.

9. The method of claim 1 and which comprises applying the bromonitromethane to the soil in the amount of between 1 and 40 quarts of bromonitromethane per acre of the soil.

10. The method of claim 9 in which said applying comprises applying the bromonitromethane to the soil by an application process selected from the group consisting of: mixing, fumigation and injection.

11. The method of claim 9 and which comprises applying the bromonitromethane in the amount of between 2 and 20 quarts of bromonitromethane per acre of the soil.

12. The method of claim 11 and which comprises applying the bromonitromethane in the amount of about 4 quarts of bromonitromethane per acre of the soil.

13. The method of claim 9 and which comprises applying the bromonitromethane in the amount of less than about 8 quarts of bromonitromethane per acre of the soil.

14. The method of claim 1 and which comprises applying the bromonitromethane to the soil in the amount of between 0.02 and 1.0 ml of bromonitromethane per kg of the soil.

15. The method of claim 14 in which said applying comprises applying the bromonitromethane to the soil by an application process selected from the group consisting of: mixing, fumigation and injection.

16. The method of claim 14 and which comprises applying the bromonitromethane in the amount of between 0.04 and 0.5 ml of bromonitromethane per kg of the soil.

17. The method of claim 16 and which comprises applying the bromonitromethane in the amount of about 0.1 ml of bromonitromethane per kg of the soil.

18. The method of claim 14 and which comprises applying the bromonitromethane in the amount of less than about 0.2 ml of bromonitromethane per kg of the soil.

19. A method for the treatment of nematodes in soil which comprises applying to the nematodes in the soil a composition including a nematicidal amount of bromonitromethane and a carrier system.

20. The method of claim 19 and which comprises applying an aqueous emulsion of the bromonitromethane.

21. The method of claim 19 and which comprises applying a composition consisting essentially of bromonitromethane and an inert carrier.

22. The method of claim 21 and which comprises applying an aqueous emulsion of the bromonitromethane.

23. The method of claim 19 and which comprises applying a composition consisting of bromonitromethane and an inert carrier.

24. The method of claim 23 and which comprises applying an aqueous emulsion of the bromonitromethane.

* * * * *